(12) United States Patent
Rogosnitzky

(10) Patent No.: US 10,226,420 B2
(45) Date of Patent: Mar. 12, 2019

(54) METHODS OF EYE TREATMENT USING THERAPEUTIC COMPOSITIONS CONTAINING DIPYRIDAMOLE

(71) Applicant: O.D. Ocular Discovery Ltd., Rehovot (IL)

(72) Inventor: Moshe Rogosnitzky, Kiryat Ye'arim (IL)

(73) Assignee: O.D. OCULAR DISCOVERY LTD, Rehovot (IL)

( * ) Notice: Subject to any disclaimer, the term of this patent is extended or adjusted under 35 U.S.C. 154(b) by 11 days.

(21) Appl. No.: 15/826,725

(22) Filed: Nov. 30, 2017

(65) Prior Publication Data

US 2018/0078501 A1 Mar. 22, 2018

Related U.S. Application Data

(60) Division of application No. 15/428,709, filed on Feb. 9, 2017, now Pat. No. 9,901,580, and a division of application No. 14/483,181, filed on Sep. 11, 2014, and a division of application No. 14/483,101, filed on Sep. 10, 2014, now Pat. No. 9,675,055, which is a continuation-in-part of application No. 13/798,154, filed on Mar. 13, 2013, now Pat. No. 9,254,289.

(51) Int. Cl.
| | | |
|---|---|---|
| *A61K 31/519* | (2006.01) | |
| *A61K 9/00* | (2006.01) | |
| *A61K 9/06* | (2006.01) | |
| *A61K 9/08* | (2006.01) | |

(52) U.S. Cl.
CPC .............. *A61K 9/0048* (2013.01); *A61K 9/06* (2013.01); *A61K 9/08* (2013.01); *A61K 31/519* (2013.01)

(58) Field of Classification Search
CPC .................................................. A61K 31/519
See application file for complete search history.

(56) References Cited

U.S. PATENT DOCUMENTS

| | | | |
|---|---|---|---|
| 3,031,450 A | 4/1962 | Fischer et al. | |
| 4,382,953 A | 5/1983 | Ishii et al. | |
| 4,912,092 A | 3/1990 | Gruber | |
| 5,424,078 A * | 6/1995 | Dziabo ............... | A01N 59/00 424/661 |
| 5,438,060 A | 8/1995 | Miyazaki et al. | |
| 5,731,432 A | 3/1998 | Erion | |
| 5,780,450 A | 7/1998 | Shade | |
| 6,300,328 B1 | 10/2001 | Klimko | |
| 7,825,102 B2 | 11/2010 | Fishman et al. | |
| 9,254,289 B2 | 2/2016 | Rogosnitzky | |
| 2003/0125299 A1 * | 7/2003 | Peterson ............ | A61K 31/00 514/47 |
| 2007/0010502 A1 | 1/2007 | Keith et al. | |
| 2007/0225217 A1 | 9/2007 | Chappell et al. | |
| 2010/0222369 A1 | 9/2010 | Fishman et al. | |

FOREIGN PATENT DOCUMENTS

| | | |
|---|---|---|
| EP | 0011654 A1 | 6/1980 |
| EP | 0011654 A1 | 6/1980 |
| EP | 0234854 B1 | 5/1991 |
| RU | 2008122978 A | 12/2009 |

OTHER PUBLICATIONS

Wang, Li Qiang & Ma, Ming, Preparation and Clinical Application of Persantine Eye Drops, Chinese Journal of Hospital Pharmacy, Dec. 1997, p. 138-139, vol. 17(3), China (Chinese language publication submitted together with English translation).
Kaminski "Pharmacology Considerations with Your Patients Over 50" presentation at AFOS Meeting Oct. 22-23, 2012 in Phoenix AZ.
Li Pharmacological modulation of cytotoxicity and cellular uptake of anti-cancer drugs by PDE5 inhibitors in lung cancer cells. Pharm Res. Jan. 2014;31(1):86-96.
Doherty "Direct effects of selective type 5 phosphodiesterase inhibitors alone or with other vasodilators on the erectileresponse in cats" J Urol. Mar. 2001;165(3):1004-9.
Boptom "Modulation of tear film protein secretion with phosphodiesterase inhibitors" Clinical and Experimental Ophthalmology (2000) 28, 208-211.
Carlock "Pterygium: Nonsurgical Treatment Using Topical Dipyridamole—A Case Report" Case Rep Ophthalmol 2014;5:98-103.
Fishman "Pharmacology and Therapeutic Applications of A3 Receptor Subtype" Current Topics in Medicinal Chemistry 2003, 3, 463-469.
Gillespie "Inhibition and Stimulation of Photoreceptor Phosphodiesterases by Dipyridamole and M&B 22,948" Molecular Pharmacology, 36:773-781.
Bell"Introduction" (Apr. 2014) Phosphodiesterases and Their Inhibitors (Wiley; eds Liras and Bell) vol. 61; chapter 1 (pp. 1-7).
Maskovsky; Medicinal Drugs( 16th edition)Publishing House "LLC RIA New Wave" Submitted for publication on Oct. 15, 2009 N.A.Litvina (ed.) vol. No. 54 Cited from chapter "Drugs Impacting Blood Coagulation and Aggregation of the Thrombocytes" pp. 485-486 (original Russian provided with English translation).
International Search Report dated Jun. 19, 2014 in PCT/IB2014/059645.
Podos, Effect of dipyridamole on prostaglandininduced ocular hypertension in rabbits, Invest. Opthalmol. Visual Sci., Jun. 1979, pp. 646-648.
PCT/US07/069440, Dec. 6, 2007, Leung.
Internet site:http://pingueculaeyedrops.com/about-the-drops-html/ [attached copy doiwnoaded Jul. 27, 2017).
Rabinovich-Guillat et al., "Cationic Vectors in Ocular Drug Delivery", Journal of Drug Targeting, Oct.-Dec. 2004, pp. 623-633, vol. 12(9-10), Taylor&Francis.

(Continued)

*Primary Examiner* — Zohreh A Fay
(74) *Attorney, Agent, or Firm* — IPAttitude Ltd.; S. Yarus

(57) ABSTRACT

A method comprising administering an effective amount of a topical dipyridamole to a subject in need thereof due to conjunctivitis.

18 Claims, No Drawings

(56) References Cited

OTHER PUBLICATIONS

Kumar et al., "Recent Challenges and Advances in Ophthalmic Drug Delivery System", The Pharma Journal 2012, pp. 1-15, vol. 1(4).
Ashton et al., "Formulation Influence on Conjunctival Penetration of Four Beta Blockers in the Pigmented Rabbit: A Comparison with Corneal Penetration", Pharmaceutical Research, 1991, pp. 1166-1174, vol. 8(9), Springer.
Abelson and Fink. "How to Handle BAK Talk", Rev Opthalmol. 2002, pp. 52-54, vol. 9 (12).
Farinelli et al. "Neuroprotective Actions of Dipyridamole on Cultured CNS Neurons", The Journal of Neurosicence, Jul. 15, 1998; pp. 5112-5123, vol. 18(14), Society for Neuroscience.
Chen et al., "Adenosine Rreceptors as Drug Targets—What are the Challenges?" Nature Reviews Drug Discovery, 2013, pp. 265-286, vol. 12, MacMillan.
Rogosnitzy et al., "Topical Dipyridamole for Treatment of Pterygium and Associated Dry Eye Symptoms: Analysis of User-Reported Outcomes", Mar. 2016, pp. 119, ARVO.
Wang and Ma, "Preparation and Clinical Application of Persantine Eye Drops, Chinese Journal of Hospital Pharmacy", Dec. 1997, pp. 138-139, vol. 17(3), Chinese language publication submitted together with English translation.
Search report in IL225279 dated Jun. 9, 2013 (original Hebrew + English translation).
Office Action in IL225279 dated Aug. 22, 2013 (original Hebrew + English translation).
Podos, "Effect of Dipyridamole on Prostaglandin Induced Ocular Hypertension in Rabbits" Invest. Ophthalmol. Visual Sci., Jun. 1979, pp. 646-648, vol. 8(16), Assoc. for Res. in in Vis. and Ophthal. Inc.
Mashovsky, "Drugs Impacting Blood Coagulation and Aggregation of the Thrombocyte", cited in "Medicinal Drugs" 16th edition, Publishing House "LLC RIA New Wave" Submitted for publication on Oct. 15, 2009, pp. 485-486, vol. 54, Editor: N.A. Litvina.
Translation Validation for NPL citations 9 & 10 above.
Skimming et al. Am J Physiol. (Feb. 1997);272(2 Pt 2):H921-6.
Bijlstra et al. Clin Pharmacol Ther. (Mar. 2004);75(3):147-56.
Skimming et al. "Effects of dipyridamole and adenosine infusions on ovine pulmonary and systemic circulations" Am J Physiol. Feb. 1997;272(2 Pt 2):H921-6 [Abstract].
Bijlstra et al. "Glyburide inhibits dipyridamole-induced forearm vasodilation but not adenosine-induced . . . " Clin Pharma. Ther. Mar. 2004;75(3):147-56 [Abstract].
Ghiardi et al. "The purine nucleoside adenosine . . . " Vision Research 1999, 39:2519.
Erion et. al., "Discovery of AMP mimetics . . . "J. Am Chem. Soc. 1999, 121:308.
Wilson & White "Intracoronary papaverine: an ideal coronaryvasodilator for studies of the coronarycirculation in conscious humans" Circulation (1986) 73(3):444-451.
Bal et al. "Mast cell density in pterygium, and its association with ultraviolet exposure in different climatic conditions . . . " Turkish Journal of Pathology 2006;22(1):11-16.
Deckert et al., Adenosine—an endogenous neuroprotective metabolite and neuromodulator, Journal of Neural Transmission, vol. 43 (suppl.), pp. 23-31 (1994)) [Abstract].
Hurmeric et al.(2013)"Single and multiple injections . . . "Clinical Ophthalmology 2013:7 467-473.
Rosenbaum et al. (1988) "Ocular inflammatory effects . . . " Amer. J. of Pathol. 133(1): 47-53.

\* cited by examiner

METHODS OF EYE TREATMENT USING THERAPEUTIC COMPOSITIONS CONTAINING DIPYRIDAMOLE

CROSS REFERENCE TO RELATED APPLICATIONS

This application is a divisional application of U.S. Ser. No. 15/428,709, currently pending, filed on Sep. 2, 2017 and having the same inventor as the present application, U.S. Ser. No. 15/428,709, is a divisional application of U.S. Ser. No. 14/483,181, abandoned, filed on Feb. 9, 2017 and having the same inventor as the present application, U.S. Ser. No. 14/483,181, filed on Sep. 11, 2014 by the same inventor and entitled Therapeutic Compositions Containing Dipyridamole and Treatment Packs Including Such Compositions and Methods for Producing Same was a continuation in part (CIP) according to 35 U.S.C. § 120 of U.S. Ser. No. 13/798,154;

U.S. Ser. No. 13/798,154 was filed Mar. 13, 2013 by the same inventor and entitled METHODS FOR TREATING EYE DISORDERS USING DIPYRIDAMOLE is now granted as U.S. Pat. No. 9,254,289, These US applications also enjoyed foreign priority from Israeli application 225179, filed 12 Mar. 2013, which is now granted.

A corresponding international application PCT IB2014/059645 filed on 11 Mar. 2014 by the same inventor and entitled "COMPOSITIONS FOR USE IN TREATING EYE DISORDERS USING DIPYRIDAMOLE, also claimed priority from Israel Application 225179;

Each of these related applications is fully incorporated herein by reference for all that it contains.

FIELD OF THE INVENTION

The various embodiments described are in the field of eye treatment.

BACKGROUND OF THE INVENTION

The medical condition referred to as "dry eye" is a disorder of the tear film due to tear deficiency or excessive tear evaporation which causes damage to the interpalpebral ocular surface associated with symptoms of ocular discomfort.

Dry eye includes two major classes: (i) aqueous tear deficient dry eye (ADDE), and (ii) evaporative dry eye (EDE).

ADDE refers mainly to a failure of sufficient tear secretion due to lacrimal dysfunction. ADDE has two major subclasses: (i) Sjogren's Syndrome dry eye (SSDE), and (ii) non-SS dry eye (such as in Graft-versus-Host Disease (GvHD) or in diabetes mellitus or non-specific dry eye).

EDE may be: (i) intrinsic, due to diseases affecting lid structures or dynamics, or (ii) extrinsic, in which ocular surface disease occurs due to some extrinsic exposure, such as topical drug preservatives, contact lens wear, pterygium, pinguecula, exposure to air conditioned environments, or vitamin A deficiency.

Alternatively or additionally, Dry eye is sometimes caused by Meibomian gland dysfunction.

The most prescribed medication for dry eye is Restasis (cyclosporine drops) with a 60% market share. This product works for 15% of patients vs 5% whom respond to placebo. It has several significant side effects and is not well tolerated.

As used in this specification and the accompanying claims the term "corneal ulcer" refers to a medical condition in which the corneal epithelium, and/or stroma are lysed. Corneal ulcers are caused, for example, by infections and/or physical force. In the case of infections, corneal ulcers often result from the activation and hypersecretion of collagenolytic enzyme. The ulcerative process is often linked to collagenolytic enzymes such as bacterial collagenase and/or matrix metalloproteases (MMPs). Corneal ulcers often result from keratitis.

Keratitis is an inflammation of cornea and is caused, for example, by contact lens wear, injury to the eye, infections and environmental causes.

Corneal abrasions are similar in etiology to corneal ulcers but are restricted to the epithelial layer of the cornea without penetration to the stroma. Corneal abrasions are also referred to as "scratch of the cornea" and may be caused by infection and/or trauma. They usually are associated with or known as superficial keratitis.

The changes in the extracellular environment caused by the degradation of stromal collagen promote ulcers. Such conditions produce a vicious circle of activation of corneal stromal cells and degradation of corneal stroma. When the bacteria are killed by antibiotics, secretion of bacterial collagenase is suppressed, and direct corneal stroma degradation due to the bacteria is suppressed. However, since most antibiotics cannot suppress activation of corneal stromal cell caused by the biological signals once transmitted from bacteria to corneal stromal cells, progression of ulcer is clinically observed from time to time.

The corneal/conjunctival diseases, including a repeated erosion of the cornea and a prolonged conical epithelial deficiency, are associated with such disorders. The repairing process of the corneal/conjunctival epithelial disorders involves the coverage of the epithelial deficiency by the migration of conical epithelial cells, followed by a subsequent cell division and differentiation, resulting in reconstitution of normal cornea and conjunctiva.

Corneal anesthesia and congenital corneal anesthesia usually develop into or are regarded as neurotrophic keratopathy. Neurotrophic keratopathy is a degenerative corneal disease induced by an impairment of the trigeminal nerve. Impairment or loss of corneal sensory innervation is sometimes responsible for conical epithelial defects, ulcers, and perforations.

A pterygium (sometimes referred to as Surfer's eye) is a non-cancerous growth that starts in the clear, thin tissue (conjunctiva) of the eye. This growth covers the white part of the eye (sclera), and extends onto the cornea. It is slightly or significantly raised, and often contains visible blood vessels (also known as hyperemia). The problem may occur in one or both eyes. Pterygium may become inflamed and cause burning, irritation, or a feeling like there's something foreign in the eye. Vision may be affected if the growth extends far enough onto the cornea. There is at present no known curative treatment for pterygium other than surgery. There is a very high recurrence rate for pterygium post surgery. Formulations of chemotherapy or immune-suppressive eye-drops (such as mitomycin or cyclosporine) are often used in the eye to prevent recurrence after surgery. Surgery often results in scarring which can affect vision. The cause of pterygium is not certain. It has been linked to prolonged sun exposure through ultraviolet induced mechanisms. It has also been linked to viral processes such as HPV. It is considered by some to be a neoplastic process or one able to transform into a cancerous condition.

A pinguecula is a yellowish, slightly-raised thickening of the conjunctiva on the sclera. According to some opinions, a pinguecula always precedes the formation of a pterygium. Pingueculae typically occur on the part of the sclera that is between the eyelids, and therefore is exposed to the sun. In some cases pingueculae become swollen and inflamed, a condition called pingueculitis. This is usually treated with topical steroids or topical anti-inflammatory drugs. Frequently, pinguecula can lead to the formation of pterygium. There is at present no known curative treatment for pinguecula other than surgery. There is a very high recurrence rate for pingueculae post surgery. Formulations of chemotherapy or immune-suppressive eye-drops (such as mitomycin or cyclosporine) are often used in the eye to prevent recurrence after surgery. Surgery often results in scarring which can affect vision.

Uveitis is inflammation of the middle layer of the eye, called the uvea or uveal tract.

The uvea consists of the middle, pigmented, vascular structures of the eye, and includes the iris, ciliary body, and choroid. Uveitis can affect the anterior segment of the eye or the posterior segment of the eye. When it affects the anterior segment, it is usually referred to as anterior uveitis. In western countries, anterior uveitis accounts for between 50% and 90% of uveitis cases, while in Asian countries the proportion drops to be between 28% and 50%. Uveitis is estimated to be responsible for approximately 10-20% of the cases of blindness in the United States. The cause of uveitis is generally infectious (bacterial or viral infection), autoimmune-disease-related, trauma related or idiopathic. Genetic factors can act as a predisposing factor for this difficult-to-treat condition. While uveitis is sometimes treated systemically, localized treatments will usually differ when treating anterior segment or posterior segment uveitis.

Blepharitis is a swelling or inflammation of the eyelids. It often contributes to dry eye syndrome and can cause many ocular symptoms such as itching, grittiness, photophobia, eyelid crusting and red, swollen eyes. Blepharitis prevalence increases with age. Amongst other factors, it may be caused by an infection, allergies or headlice. It is often associated with Meibomian gland dysfunction. It is typically treated using antibiotics or anti-inflammatory drugs such as steroids or a combination of both.

Pink eye, also referred to as conjunctivitis, madras eye, red eye, allergic conjunctivitis or non-specific conjunctivitis is a redness and swelling of the conjunctiva often resulting from inflammation or infection. It is often treated using antibiotics or anti-inflammatory drugs including steroids.

Keratoconus is a degenerative (thinning) disorder of the cornea that causes visual distortion. It is typically treated with various kinds of contact lenses that correct vision, with plastic rings inserted into the midlayer of the cornea to flatten it or with corneal crosslinking. In advanced cases corneal transplant surgery becomes necessary.

In the prior art, dipyridamole {2,6-bis (diethanolamino)-4,8-dipiperidinopyrimido [5,4-d] pyrimidine}, closely related substituted pyrimido-pyrimidines, and their preparation are taught by Fischer in U.S. Pat. No. 3,031,450 (hereinafter referred to as Fischer '450). Dipyridamole was introduced as a coronary vasodilator in the early 1960s, and is well known to have platelet aggregation inhibitor properties due to the inhibition of adenosine uptake. Subsequently, dipyridamole was shown to reduce thrombus formation in a study of arterial circulation of the brain in a rabbit model. These investigations led to its use as an anti-thrombotic agent. Dipyridamole soon became the therapy of choice for such applications as stroke prevention, maintaining the patency of coronary bypass and valve-replacement, as well as for treatment prior to coronary angioplasty.

In Patent Publication No. EP 0234854 B1 by Gilbard et al. (hereinafter referred to as Gilbard '854), it is suggested that cyclic cAMP functions as a second messenger for exocytosis in the lacrimal gland, and acts to increase tear secretion. cAMP is degraded by phosphodiesterases. It is therefore thought that suppressing phosphodiesterases can result in increased intracellular cAMP levels, and thus enhance tear secretion. Dipyridamole is believed to act as a phosphodiesterase inhibitor in some human cells, and is thought to exert some of its cardiovascular benefits via this mechanism.

However, on page 19 of Patent Publication No. WO 2007/140181 by Leung (hereinafter referred to as Leung '181), it is disclosed that there was a negligible effect on cAMP levels after the addition of dipyridamole in comparison to a control. Only a combination of caffeine and dipyridamole yielded the desired effect of decreasing cAMP in-vitro, which is assumed to indicate increased cellular uptake of cAMP through upregulation of the adenosine-3 receptor.

In WO 2010056710, Defterios teaches that dipyridamole increases nitric oxide levels thus precluding its use as single agent therapy for treating inflammatory eye disorders. Defterios teaches to overcome this problem through combining benzisoselenazole with dipyridamole since benzisoselenazole may decrease nitrix oxide (NO) formed during treatment with dipyridamole resulting in tolerability of a therapeutically effective amount. Thus Defterios teaches against the use of dipyridamole monotherapy for eye disorders.

Podos (in Invest. Opthalmol Visual Sci. June 1979 p. 646-648) investigated the effect of dipyridamole in treatment of ocular inflammatory disease. He found that systemically administered dipyridamole had a significant beneficial effect however topically administered dipyridamole (in liquid formulation) was ineffective.

SUMMARY OF THE INVENTION

One aspect of some embodiments of the invention relates to dipyridamole based compositions for use in treating anterior segment eye disorders. In some exemplary embodiments of the invention, dipyridamole applied topically to the eye (e.g. as drops, ointment or cream) alleviates symptoms of inflammatory eye conditions.

Anterior segment eye disorders affect the conjunctiva, cornea, uvea, iris, lens, sclera, eyelid, Meibomian gland and/or lacrimal system. These tissues are physiologically different from those found in the posterior segment of the eye (e.g. optic nerve and retina). As used in this specification and the accompanying claims the term "dipyridamole" includes pharmaceutically acceptable salts thereof.

Another aspect of some embodiments of the invention relates to treatment packs containing such dipyridamole compositions, packaging materials and instructions specifying a suitable dosage regimen for treatment of one or more specific anterior segment eye disorders. According to various exemplary embodiments of the invention the eye disorders are selected from the group consisting of ADDE and EDE.

Another aspect of some embodiments of the invention relates to dipyridamole with a concentration so dilute that it falls into the classification of a homeopathic preparation. Surprisingly, homeopathic concentrations of dipyridamole applied to the eye provide real and significant therapeutic benefits as demonstrated in Examples presented hereinbelow. In some exemplary embodiments of the invention, the low concentrations may contribute to a reduction in undesirable increases in nitric oxide levels and/or obviates a need for co-administration with benzisoselenazole or other NO inhibitors.

Such compositions and treatment indications would, inter alia, overcome the problems mentioned above associated with such ailments.

In some exemplary embodiments of the invention, dipyridamole is the main therapeutic agent in the composition and does not benefit from any synergistic effect with an additional therapeutic agent. In some embodiments, dipyridamole is the sole therapeutic agent in the composition.

In some embodiments, dipyridamole is provided in a composition without caffeine.

In some embodiments, dipyridamole is provided in a composition without corticosteroids.

In some embodiments, dipyridamole is provided in a composition without benzisoselenazoles (e.g. ebselen).

In some embodiments, the aggregate daily dosage of dipyridamole administered is 0.5 mg per day or less.

In some embodiments, dipyridamole is used without concurrently or within 14 days administering amoxapine and/or sertraline and/or dipivefrin and/or prostaglandin E and/or rolipram.

In some embodiments, dipyridamole is used without HDAC inhibitors and/or additional anti-VEGF compounds and/or HMG-CoA reductase inhibitors such as statins and/or nitric oxide (NO) inhibitors.

It will be appreciated that the various aspects described above relate to solution of technical problems associated with treatment of anterior segment eye disorders.

Alternatively or additionally, it will be appreciated that the various aspects described above relate to solution of technical problems related to application of a known active ingredient to new clinical uses.

In some exemplary embodiments of the invention there is provided a composition including: (a) a physiologically effective amount of dipyridamole formulated for treatment of the anterior segment of the eye of a subject suffering from an anterior segment eye disorder; and (b) a physiologically acceptable carrier. In some embodiments, the composition according is formulated as a solution. In other exemplary embodiments of the invention, the composition is formulated as a cream or ointment. Alternatively or additionally, in some embodiments the physiologically effective amount of dipyridamole includes a concentration of at least about $10^{-6}$ molar (moles/liter). Alternatively or additionally, in some embodiments the composition includes 200 µg/ml or less of dipyridamole. Alternatively or additionally, in some embodiments the composition includes 100 µg/ml or less of dipyridamole. Alternatively or additionally, in some embodiments the composition does not include a physiologically active concentration of any member of the group consisting of caffeine, a corticosteroid, a benzisoselenazole (e.g. ebselen), amoxapine, sertraline, dipivefrin, prostaglandin E, rolipram, an HDAC inhibitor, an additional anti-VEGF compound, and an HMG-CoA reductase inhibitor (e.g. a statin) and/or nitric oxide (NO) inhibitor.

In some exemplary embodiments of the invention there is provided a treatment pack including: (a) multiple doses of a composition containing dipyridamole as an active ingredient; (b) packaging material; and (c) instructions for topical administration of the composition to the anterior segment of the eye to treat an anterior segment eye disorder. According to various exemplary embodiments of the invention, the composition is formulated as a solution a cream or an ointment. Alternatively or additionally, in some embodiments the composition does not include a physiologically effective amount of any member of the group consisting of caffeine, a corticosteroid, a benzisoselenazole (e.g. ebselen), amoxapine, sertraline, dipivefrin, prostaglandin E, rolipram, an additional anti-VEGF compound, and an HMG-CoA reductase inhibitor (e.g. a statin) and/or nitric oxide (NO) inhibitors if the instructions are followed. Alternatively or additionally, in some embodiments the composition contains dipyridamole at a concentration of at least about $10^{-6}$ molar (moles/liter). Alternatively or additionally, in some embodiments the instructions specify administration of the composition to the eye(s) of a subject at least once every other day. Alternatively or additionally, in some embodiments the instructions specify a dosing regimen which leads to an aggregate daily dosage of dipyridamole of 0.5 mg per day or less. Alternatively or additionally, in some embodiments the treatment pack includes a single container for the multiple doses. Alternatively or additionally, in some embodiments the treatment pack includes multiple containers, each of the multiple containers containing a single dose of the multiple doses.

In some exemplary embodiments of the invention there is provided a method including: (a) adjusting the pH of a physiologically acceptable ophthalmologic solution to between about 5.5 and about 6.8; (b) dissolving dipyridamole in the solution at a concentration of 5 µg/ml to 200 µg/ml; and (c) sterilizing the resultant dipyridamole composition. In some exemplary embodiments of the invention, the method includes titrating the solution to achieve the pH of about 6.7. Alternatively or additionally, in some embodiments the dissolving includes dissolving at a concentration of at least 85 µg/ml. Alternatively or additionally, in some embodiments the method includes packaging the sterilized dipyridamole composition in container configured to deliver drops to the eye. Alternatively or additionally, in some embodiments the method includes assembling a treatment pack including the container, packaging material and instructions for topical administration of the composition to the eye to treat an anterior segment eye disorder in a subject in need thereof.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, actions or components without precluding the addition of one or more additional features, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

DETAILED DESCRIPTION OF EMBODIMENTS

Embodiments of the invention relate to therapeutic compositions containing dipyridamole and treatment packs including such compositions and methods for producing such treatment packs and/or compositions.

Specifically, some embodiments of the invention can be used to treat anterior segment eye disorders such as dry eye including aqueous tear deficient dry eye (ADDE) and/or evaporative dry eye (EDE) and all dry eye variations as described hereinabove. Thus, "anterior segment eye disorder" includes, but is not limited to, scleritis and/or Graft-versus-Host Disease (GvHD) and/or keratitis and/or corneal ulcer and/or corneal abrasion and/or Thygeson's superficial punctuate keratopathy and/or corneal neovascularization and/or Fuch's dystrophy and/or keratoconus and/or keratoconjunctivitis sicca (dry eye) and/or iritis and/or corneal anesthesia and/or neurotrophic keratopathy and/or red eye and/or pink eye and/or keratomycosis and/or xeropthalmia and/or anterior uveitis and/or pterygium and/or keratopathy and/or pinguecula and/or blepharitis and/or Meibomian gland dysfunction.

Before explaining at least one embodiment of the invention in detail, it is to be understood that the invention is not limited in its application to the details set forth in the following description or exemplified by the Examples. The invention is capable of other or of being practiced or carried out in various ways. Also, it is to be understood that the phraseology and terminology employed herein is for the purpose of description and should not be regarded as limiting.

Physiology of Dipyridamole

Dipyridamole is readily absorbed from the gastrointestinal tract, reaching peak levels in humans 1-3 hours following oral administration. Peak plasma levels are dose dependent and range from about 0.5 g/mL after a 25 mg dose to 1.6 g/mL after a 75 mg dose. Blood levels are quite variable, possibly depending on food intake and gastrointestinal peristalsis. Ingestion on an empty stomach may result in higher blood levels. Following intravenous (IV) administration, the distribution half-life in humans is about 25 minutes, and after oral administration, is about 3 hours. When plasma levels of drug are followed for up to 60 hours after IV or oral administration of 20-50 mg, plasma levels decline tri-exponentially with half-lives of 5 minutes (IV only), 53 minutes, and about 10-12 hours. The volume of distribution is about 140 L with about 92 to 99% binding to plasma proteins, primarily alpha1-acid glycoprotein. Typical daily oral doses of dipyridamole range from 100-400 mg.

Technical Problem

Dipyridamole is practically insoluble in water (water solubility is 8.17 mg/L (Meylan, W M ET AL. (1996))), and very soluble in methanol. This creates a challenge for finding a suitable method for ocular application in which an aqueous solution delivered via single drops may contribute to patient compliance with a dosing regimen.

Exemplary Solution to Technical Problem

According to various exemplary embodiments of the invention compositions and/or treatment packs and/or methods of manufacture contribute to treatment of anterior segment eye disorders using dipyridamole at relatively high concentrations. It was determined that by adjusting the pH of the aqueous solution to ~6.6 (6.5-6.7), dipyridamole fully dissolves in the aqueous solution. The natural pH of tear fluid is 7.4; however, discomfort for the user will not be felt as long as the pH of the administered medication stays in the range of 6.6-7.8 (Sampath Kumar et al., "Recent Challenges and Advances in Ophthalmic Drug Delivery System," in *The Pharma Innovation*, Vol. 1, No. 4 (2012)). Others administer eye drops at a pH of 5.5 and find this pH to be optimal.

Other methods may be used to achieve water solubility such as ultrasonic mixing, or dissolving dipyridamole in methanol, chloroform, acetic acid, DMSO, or other carriers in which the dipyridamole is soluble, followed by adding water or saline, and then removing all or part of the carrier. Another method involves grinding the compound to a nanoparticle size prior to mixing in water/saline. It should be noted that when preparing the more dilute Exemplary Formulations C and D described below, less acidification was required. In some embodiments, acidification of the carrier to achieve solubility is achieved by addition of other acidulants commonly used in eye drops such as hydrochloric acid. Alternatively or additionally, in some embodiments sodium hydroxide is used to adjust pH. While aqueous solutions are one possibility for ocular instillation, preparing the dipyridamole in an oil or cream base is another method to overcome the aqueous solubility challenge.

Dipyridamole was found to be effective in treating ocular medical conditions when applied topically in physiological saline formulations. Topical application of dipyridamole may serve to treat dry eye caused by, for example, Graft-versus-Host Disease (GvHD), diabetes, allergic conjunctivitis, contact lens-related dry eye, and Sjogren's syndrome.

In an exemplary embodiment of the present invention, topical dipyridamole may also be used to treat corneal abrasions or ulcers resulting from, for example: viral infection, bacterial infection, fungal infection, injury resulting from wearing contact lenses, traumatic injury, and parasite infection. Moreover, topical dipyridamole may also be used for the treatment of keratitis, pterygium, pinguecula, corneal anesthesia, and corneal neovascularization.

Therefore, according to some embodiments, there is provided for the first time a composition for use in treating eye disorders, the composition including: (a) an effective amount of a topically-administered dipyridamole. In some embodiments, the topically-administered dipyridamole is formulated as an ophthalmologic solution. In some embodiments, the effective amount corresponds to a concentration of at least about $10^{-6}$ molarity. In some embodiments, the effective amount corresponds to a concentration of at least about $10^{-5}$ molarity. Alternatively or additionally, in some embodiments the effective amount is based on a treatment administration of at least once every other day. These and further embodiments will be apparent from the detailed description and examples that follow.

Some exemplary embodiments of the invention relate to compositions for use in treating eye disorders using dipyridamole. The aspects, uses, and advantages for such compositions may be better understood with reference to the accompanying description. The description is not to be taken in a limiting sense, but is made merely for the purpose of illustrating the general principles of the various embodiments of the invention. Exemplary embodiments of the present invention are detailed below in the following exemplary formulations and/or experimental examples.

Exemplary Compositions

Some embodiments of the invention relate to a therapeutic composition for ophthalmologic use. In some embodiments, the composition a physiologically effective amount of dipyridamole formulated for treatment of the anterior segment of the eye of a subject suffering from an anterior segment eye disorder and a physiologically acceptable carrier.

As used in this specification and the accompanying claims the term "physiologically acceptable carrier" indicates suitability for ocular administration. Exemplary carrier ingredients include, but are not limited to, water, saline solution, chelating agents (e.g. EDTA and/or EGTA), boric acid, preservatives, and pH adjusting agents (e.g. acids and/or bases).

As used in this specification and the accompanying claims the term "anterior segment" indicates the conjunctiva, cornea, ocular surface, uvea with iris, lens, the lacrimal system and the eyelid.

In some embodiments, dipyridamole is the sole agent in the composition present in a therapeutically effective amount.

According to various exemplary embodiments of the invention the composition is formulated as a solution, cream or an ointment.

In some embodiments, the concentration of dipyridamole in the composition is of at least about $10^{-6}$ molar (moles/liter). Alternatively or additionally, in some embodiments the composition includes 500 µg/ml, 400 µg/ml, 300 µg/ml, 200 µg/ml, 100 µg/ml, 50 µg/ml, 40 µg/ml, 30 µg/ml, 20 µg/ml, 10 µg/ml or 5 µg/ml or lesser or intermediate amounts of dipyridamole.

According to various exemplary embodiments of the invention the composition does not include a physiologically active concentration of caffeine and/or a corticosteroid and/or a benzisoselenazole (e.g. ebselen) and/or amoxapine and/or sertraline and/or dipivefrin and/or prostaglandin E, and/or rolipram, and/or an HDAC inhibitor, and/or an additional anti-VEGF compound, and/or an HMG-CoA reductase inhibitor such as a statin and/or nitric oxide (NO) inhibitors.

Exemplary Treatment Packs

Some embodiments of the invention relate to a treatment pack including multiple doses of a composition containing dipyridamole as an active ingredient, packaging material and instructions for topical administration of the composition to the anterior segment of the eye to treat an anterior segment eye disorder. According to various exemplary embodiments of the invention the packaging material is configured as a box and/or a blister pack and/or a bottle. In some embodiments, the bottle is a squeeze bottle with an integral dropper. In other exemplary embodiments of the invention, the bottle is provided with a separate dropper (e.g. fashioned as part of the cap). According to various exemplary embodiments of the invention the composition is provided as a solution and/or a cream and/or an ointment.

In some embodiments, the composition does not include a physiologically active concentration of caffeine and/or a corticosteroid and/or a benzisoselenazole (e.g. ebselen) and/or amoxapine and/or sertraline and/or dipivefrin and/or prostaglandin E, and/or rolipram, and/or an HDAC inhibitor, and/or an additional anti-VEGF compound, and/or an HMG-CoA reductase inhibitor such as a statin and/or nitric oxide (NO) inhibitor.

In some embodiments, dipyridamole is the sole agent in the composition present in a therapeutically effective amount.

In some embodiments, the composition contains dipyridamole at a concentration of at least about $10^{-6}$, or at least about $10^{-5}$, molar (moles/liter). Alternatively or additionally, in some embodiments the instructions specify administration of the composition to the eye(s) of a subject at least once every other day. According to various exemplary embodiments of the invention the instructions specify administration of the composition to the eye(s) of a subject once, twice, three, four or more times daily.

In some embodiments, the instructions specify a dosing regimen which leads to an aggregate daily dosage of dipyridamole of 0.5 mg, 0.4 mg, 0.3 mg, 0.1 mg, 0.1 mg, 0.05 mg or 0.025 mg per day or lesser or intermediate amounts.

According to various exemplary embodiments of the invention the treatment pack includes a single container for the multiple doses and/or multiple containers, each of each of the multiple containers containing a single dose of the multiple doses.

Exemplary Methods

Some embodiments of the invention relate to a production method. In some embodiments, the method includes adjusting the pH of a physiologically acceptable ophthalmologic solution to between about 5.5 and about 6.8 and dissolving dipyridamole in the solution at a concentration of 5 µg/ml to 200 µg/ml and sterilizing the resultant dipyridamole composition. According to various exemplary embodiments of the invention sterilization is by filtration and/or heating.

In some embodiments, the method includes titrating the solution to achieve a pH of about 6.7. According to various exemplary embodiments of the invention titration is with citric acid and/or hydrochloric acid and/or sodium hydroxide and/or other acids and/or bases.

In some embodiments, the dissolving includes dissolving at a concentration of at least 85 µg/ml.

In some embodiments, the method includes packaging the sterilized dipyridamole composition in a container configured to deliver drops to the eye. According to various exemplary embodiments of the invention the container is configured as a squeeze bottle, as a bottle with a dropper incorporated into the cap or as single use packets, In some embodiments, the method includes assembling a treatment pack including the container, packaging material and instructions for topical administration of the composition to the eye(s) to treat an anterior segment eye disorder.

Exemplary Dosages

According to various exemplary embodiments of the invention the daily dosage of dipyridamole administered to a subject is 2 µg, 5 µg, 10 µg, 15 µg, 20 µg, 25 µg, 50 µg, 75 µg, 100 µg, 200 µg, 300 µg, 400 µg, 500 µg, 600 µg, 750 µg, 1 mg, 1.5 mg, 1.75 mg, 2.0 mg, 2.5 or 5 mg or intermediate or lesser amounts. In cases where only 1 eye requires treatment, the dosage is halved. According to various exemplary embodiments of the invention the daily dosage is administered all at once, according to a twice daily regimen, a three times daily regimen or a four or more times daily regimen.

In some embodiments, liquid formulations are administered as 1-2 drops (~50-100 µL)/eye at each administration.

In other exemplary embodiments of the invention, a cream or ointment formulation is administered at 0.05 to 0.3 ml/eye at each administration.

Exemplary Concentrations

According to various exemplary embodiments of the invention the concentration of dipyridamole in a composition administered to the eye is 2 µg, 3 µg, 4 µg, 5 µg, 10 µg, 15 µg, 25 µg, 50 µg, 100 µg, or 200 µg, 500 µg, 1000 µg or 2000 µg per ml. In some embodiments, cream or ointment formulations employ a lower concentration than liquid formulations.

It is expected that during the life of this patent many ophthalmologically acceptable carriers will be developed and the scope of the invention is intended to include all such new technologies a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Alternatively or additionally, various exemplary embodiments of the invention exclude any specific feature, part, component, ingredient, process or element which is not specifically disclosed herein.

Specifically, the invention has been described in the context of drops and ointments but might also be used as a cream or emulsion.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Exemplary Formulation A

Dipyridamole eye drops were prepared as follows. 1 g of citric acid was mixed in 100 mL saline (0.9% w/v sodium chloride in sterile water) to obtain a pH of 6.7. 8.5 mg of dipyridamole was weighed, irradiated by UVB for 30 minutes for sterility, and diluted in the 100 mL saline. This solution was then filtered through a 0.22 micron filter for sterilization, resulting in a solution containing 85 µg of dipyridamole per mL. Using a dropper, one drop (equivalent to approximately 0.05 mL) was applied to the eye.

Exemplary Formulation B

Dipyridamole eye drops were prepared as follows. 1 g of citric acid was mixed in 100 mL saline (0.9% w/v sodium chloride in sterile water) to obtain a pH of 6.7. 4.25 mg of dipyridamole was weighed, irradiated by UVB for 30 minutes for sterility, and diluted in the 100 mL saline. This solution was then filtered through a 0.22 micron filter for sterilization, resulting in a solution containing 42.5 µg of dipyridamole per mL. Using a dropper, one drop (equivalent to approximately 0.05 mL) was applied to the eye.

Exemplary Formulation C

Dipyridamole eye drops were prepared as follows. 1 g of citric acid was mixed in 100 mL saline (0.9% w/v sodium chloride in sterile water) to obtain a pH of 6.7. 2.125 mg of dipyridamole was weighed, irradiated by UVB for 30 minutes for sterility, and diluted in the 100 mL saline. This solution was then filtered through a 0.22 micron filter for sterilization, resulting in a solution containing 21.25 µg of dipyridamole per mL. Using a dropper, one drop (equivalent to approximately 0.05 mL) was applied to the eye.

Exemplary Formulation D

Dipyridamole eye drops were prepared as follows. 1 g of citric acid was mixed in 100 mL saline (0.9% w/v sodium chloride in sterile water) to obtain a pH of 6.7. 1.0625 mg of dipyridamole was weighed, irradiated by UVB for 30 minutes for sterility, and diluted in the 100 mL saline. This solution was then filtered through a 0.22 micron filter for sterilization, resulting in a solution containing 10.625 µg of dipyridamole per mL. Using a dropper, one drop (equivalent to approximately 0.05 mL) was applied to the eye.

Appropriate and accepted methodologies for measurement of improvement in the various described conditions were applied whenever possible in order to avoid relying only on patient-reported improvement. These methodologies included where appropriate corneal or rose-bengal staining, Schirmer's test, tonometry, fluorescein staining, tear film breakup time, refractometer, slit lamp examination and similar techniques.

Example 1: GvHD Treatment

Five human males suffering from GvHD-related dry eye were treated with one drop of Formulation A bilaterally twice daily. Subjective relief from the dry-eye symptoms was attained within half an hour. The patients required subsequent application twice daily. After 3 days of use, redness in the eye (or pink eye) disappeared.

Example 2: Diabetes-Related Dry Eye Treatment

In a first experiment, two human females suffering from diabetes-related dry eye were treated with one drop of Formulation C bilaterally twice daily. Relief from the dry-eye symptoms was attained within an hour. The patients required subsequent application twice daily. After 5 days of use, redness in the eye (or pink eye) disappeared.

In a second experiment, a human female suffering from diabetes-related dry eye was treated with one drop of Formulation B bilaterally once every other day. Relief from the dry-eye symptoms was attained within twenty minutes. The patient required subsequent application once every other day. After 10 days of use, redness in the eye (or pink eye) disappeared. Maintenance continued with administration once every other day.

In a third experiment, four human males suffering from diabetes-related dry eye were treated with one drop of Formulation A bilaterally twice daily. Relief from the dry-eye symptoms was attained on average within half an hour. The patients required subsequent application twice daily. After an average of one week of use, redness in the eye (or pink eye) completely disappeared.

Example 3: Corneal Ulcer

In a first experiment, a human male suffering from a viral eye infection with corneal ulcer was treated with one drop of Formulation B bilaterally twice daily. Exudation ceased within 8 hours. The patient required subsequent application twice daily. After 4 days of use, redness in the eye (or pink eye) disappeared, and the eye was completely healed within 5 days.

In a second experiment, two human males suffering from a viral eye infection with corneal abrasion (i.e., the onset of a corneal ulcer) were treated with one drop of Formulation A bilaterally twice daily. Exudation ceased within 5 hours. The patients required subsequent application twice daily. After 2-3 days of use, redness in the eye (or pink eye) disappeared, and the eyes were completely healed within 5-6 days.

In a third experiment, a human female suffering from a conical ulcer in one eye was treated with one drop of Formulation A twice daily. Relief from pain and irritation was attained within one day. The patient required subsequent application twice daily. After 7 days of use, the ulcer had healed completely.

Example 4: Pterygium

In a first experiment, a human male suffering in one eye from pterygium, with related dry eye and pink eye, was treated with one drop of Formulation B twice daily. Relief from the dry-eye symptoms was attained within one day. The patient required subsequent application twice daily. After 10 days of use, redness in the eye (or pink eye) disappeared. After 6 weeks of use, the pterygium shrank by about half its size, and continued to decrease in size with ongoing use.

In a second experiment, a human female suffering in one eye from pterygium, with related dry eye and inflammation, was treated with one drop of Formulation C twice daily. Relief from the dry-eye symptoms was attained within two days. The patient required subsequent application twice daily. After 8 weeks of use, the pterygium shrank to about half its size, and continued to decrease in size with ongoing use.

Example 5: Deep Corneal Ulcer

A human male suffering from a deep corneal ulcer with stromal involvement in one eye was treated with one drop of Formulation A three times daily. Relief from pain and irritation was attained within 24 hours. The patient required subsequent application twice daily. After 7 days of use, the cornea had completely reepithelialized.

Example 6: Neurotrophic Keratopathy

Three females suffering from diabetes-related corneal anesthesia (neurotrophic keratopathy) were treated with one drop of Formulation C daily. Symptoms of corneal anesthesia began improving within 2-3 days. The patients required subsequent application twice daily. After about 3 weeks of use, the patients reported complete relief of symptoms.

Two females suffering from diabetes-related conical anesthesia were treated with one drop of Formulation A daily. Symptoms of corneal anesthesia started improving within 2 days. After approximately one week of use, the patients reported complete relief of symptoms.

Example 7: Diabetes-Related Neovascularization

In a first experiment, one male suffering from diabetes-related neovascularization was treated with one drop of Formulation A twice daily. When examined after 4 weeks of use, the abnormal vessels were no longer visible by slit-lamp examination.

In a second experiment, a human male suffering from diabetes-related neovascularization was treated with one drop of Formulation C twice daily. The patient required subsequent application twice daily. When examined after 16 days of use, the abnormal vessels were no longer visible by slit-lamp photography examination.

Example 8: GvHD-Related Dry Eye

In a first experiment, six human patients suffering from GvHD-related dry eye were treated with one drop of Formulation C bilaterally twice daily. Relief from the dry-eye symptoms was attained within one hour. The patients required subsequent application twice daily. After an average of one week of use, redness in the eye (or pink eye) disappeared.

In a second experiment, three human patients suffering from GvHD-related dry eye were treated with one drop of Formulation D bilaterally twice daily. Relief from the dry-eye symptoms was attained within one hour. The patients required subsequent application twice daily. After an average of one week of use, redness in the eye (or pink eye) disappeared.

Example 9: Anterior Uveitis

In a first experiment, human male suffering from anterior uveitis in both eyes was treated with one drop of Formulation C three times daily. Relief from pain was attained within three days. Blurred vision was resolved within 7 days.

Inflammation appeared to be completely resolved within 14 days. The patient continued subsequent application twice daily to maintain remission.

In a second experiment, a human male suffering from anterior uveitis in both eyes was treated with one drop of Formulation B three times daily. Relief from pain was attained within two days. Blurred vision was resolved within 14 days. Inflammation appeared to be completely resolved within 18 days. The patient continued subsequent application twice daily to maintain remission.

Example 10: Keratoconus

A human male suffering from severe keratoconus in the left eye resulting in severe astigmatism necessitating a cylinder of 4.5 was treated using Formulation B once daily. After two months of treatment, an eye test revealed a need for cylinder correction reduction by 2 points.

Additional Exemplary Formulations

Dipyridamole eye drops were prepared by dissolving dipyridamole in sterile water. pH was adjusted as needed. According to various exemplary embodiments of the invention pH adjustment was with citric acid and/or hydrochloric acid and/or sodium hydroxide to achieve solubility. Several concentrations were prepared, ranging from 5 µg/ml to 200 µg/ml. Sterile procedures were followed.

Dipyridamole eye ointment was prepared by mixing dipyridamole in a base of yellow soft paraffin, liquid paraffin and wool fat at a ratio of (8:1:1). Several concentrations were prepared, ranging from 5 µg/ml to 200 µg/ml. Sterile procedures were followed.

Either the dipyridamole eye drops (one drop [approximately 0.05 ml] once to three times daily) or the dipyridamole eye ointment (approximately 0.1-0.3 ml [once to twice daily]) was administered to the eyes of subjects suffering from Sjogren's related dry eye, non-specific keratitis, keratoconus or allergic conjunctivitis. The concentrations used were gradually increased as tolerated. Results are presented in the following examples.

Example 11: Sjogren's Related Dry Eye

A slight transient stinging sensation was experienced upon application of the drops/ointment. Partial relief of dry eye symptoms set in within one hour of application. The relief became complete after about seven days of continuous use and continues with daily administration in some patients and periodic (every 3-4 days) administration in others.

Example 12: Non-Specific Keratitis

A slight transient stinging sensation was experienced upon application of the drops/ointment. A lowered intensity of pain was experienced within 1-2 hours of application. The relief of pain became complete after 3-4 periodic applications (spaced several hours apart) of the drops/ointment. Complete resolution of keratitis was achieved within 2-7 days of ongoing application.

Example 13: Keratoconus (Astigmatism)

Daily administration (once to twice daily) for three months led to an improvement in astigmatism enabling lowering of cylinder by a quarter to half a number in two subjects.

Example 14: Conjunctivitis (Non-Specific)

A slight transient stinging sensation was experienced upon application of the drops/ointment. Partial relief of conjunctivitis symptoms (itchiness, burning or excessive tearing) set in within one hour of application. Application continued once to twice daily. After two to four days of use all symptoms including exudation had relieved.

The invention claimed is:

1. A method comprising:
    administering an effective amount of a topical dipyridamole to a subject in need thereof due to conjunctivitis.
2. A method according to claim 1, wherein said conjunctivitis has been diagnosed as pink eye.
3. A method according to claim 1, wherein said conjunctivitis is caused by a virus.
4. A method according to claim 1, wherein said conjunctivitis is caused by bacteria.
5. A method according to claim 1, wherein said topical dipyridamole comprises 10-500 µg/ml of dipyridamole.
6. A method according to claim 1, wherein said administering comprises administering less than 1 mg per day per eye of dipyridamole.
7. A method according to claim 1, wherein said administering comprises administering less than 100 µg per day per eye of dipyridamole.
8. A method according to claim 1, wherein said topical dipyridamole has a pH≥5.5.
9. A method according to claim 1, wherein said topical dipyridamole has a pH≤6.8.
10. A method of treating conjunctivitis in a subject in need thereof comprising:
    topically administering to the eye a physiologically effective amount of a dipyridamole.
11. A method according to claim 10, wherein said conjunctivitis has been diagnosed as pink eye.
12. A method according to claim 10, wherein said conjunctivitis is caused by a virus.
13. A method according to claim 10, wherein said conjunctivitis is caused by bacteria.
14. A method according to claim 10, wherein said dipyridamole comprises 10-500 µg/ml of dipyridamole.
15. A method according to claim 10, wherein said administering comprises administering less than 1 mg per day per eye of dipyridamole.
16. A method according to claim 10, wherein said administering comprises administering less than 100 µg per day per eye of dipyridamole.
17. A method according to claim 10, wherein said topical dipyridamole has a pH≥5.5.
18. A method according to claim 10, wherein said topical dipyridamole has a pH≤6.8.

* * * * *